United States Patent
Drewes et al.

[11] Patent Number: 5,284,820
[45] Date of Patent: Feb. 8, 1994

[54] HERBICIDAL SUBSTITUTED CYCLOALKENES

[75] Inventors: Mark-Wilhelm Drewes; Peter Müller, both of Langenfeld; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 939,187

[22] Filed: Sep. 2, 1992

[30] Foreign Application Priority Data

Sep. 9, 1991 [DE] Fed. Rep. of Germany ........ 4129876

[51] Int. Cl.$^5$ .................. A01N 43/54; C07D 239/60; C07D 239/52
[52] U.S. Cl. .................. 504/243; 504/242; 504/239; 544/301; 544/302; 544/303; 544/304; 544/311; 544/312; 544/313; 544/314; 544/309; 544/315; 544/316; 544/317; 544/318; 544/321; 544/323; 544/327; 544/329; 544/330; 544/332; 544/334
[58] Field of Search ............... 544/122, 123, 295, 296, 544/301, 304, 313, 315, 318, 327, 332; 504/243, 242

[56] References Cited

U.S. PATENT DOCUMENTS 4,973,354 11/1990 Hataraka et al. ................ 71/92

Primary Examiner—John M. Ford

[57] ABSTRACT

Herbicidal substituted cycloalkenes of the formula

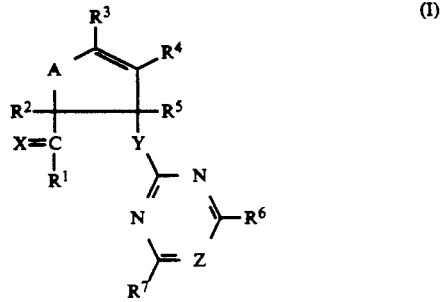

in which
A is a straight-chain or branched, optionally substituted alkanediyl group,
X is O, S, N—$R^8$ or $CR^9R^{10}$,
Y is O, S, NH or N-alkyl,
Z is N or $R^{11}$, and
$R^1$ to $R^{11}$ represent various organic radicals.

17 Claims, No Drawings

HERBICIDAL SUBSTITUTED CYCLOALKENES

The invention relates to new substituted cycloalkenes, to a process for their preparation, and to their use as herbicides.

Substituted cycloalkenes have hitherto not been important as herbicides.

There have now been found new substituted cycloalkenes of the general formula (I)

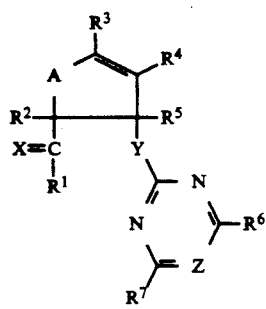

in which

A represents straight-chain or branched, optionally substituted alkanediyl, $R^1$ represents hydrogen, hydroxyl, amino, or a radical from the series comprising alkyl, alkoxy, alkylthio, alkylamino or dialkylamino, each of which is optionally substituted, $R^2$, $R^3$, $R^4$ and $R^5$ are identical or different and represent hydrogen, hydroxyl, amino, cyano, halogen, alkyl, halogenoalkyl, alkoxy, alkylthio, aryl, alkoxycarbonyl or alkoxycarbonylalkyl, $R^6$ and $R^7$ are identical or different and represent hydrogen, halogen or a radical from the series comprising alkyl, alkoxy, alkylthio, alkylamino or dialkylamino, each of which is optionally substituted, x represents oxygen sulphur or one of the groups below

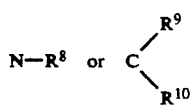

where $R^8$ represents hydrogen, hydroxyl, amino, or a radical from the series comprising alkyl, alkenyl, alkynyl, alkoxy, alkenyloxy, alkoxycarbonylalkoxy, alkylamino, dialkylamino, alkylcarbonylamino, alkoxycarbonylamino, alkylsulphonylamino, aryl, aralkyl, aryloxy, aralkyloxy,, arylamino, aralkylamino, N-alkyl-N-arylamino, hetarylamino, hetarylcarbonylamino, arylcarbonylamino or arylsulphonylamino, each of which is optionally substituted, $R^9$ represents hydrogen, halogen, cyano, carboxyl, alkoxycarbonyl, alkylcarbonylamino or dialkoxyphosphoryl and $R^{10}$ represents formyl, cyano, carboxyl, hydroxymethyl, carbamoyl, or a radical from the series comprising alkoxycarbonyl, cycloalkoxycarbonyl, alkylthiocarbonyl, alkylaminocarbonyl, cycloalkylaminocarbonyl, dialkylaminocarbonyl, alkylaminocarbonylalkoxycarbonyl, dialkylaminocarbonylalkoxycarbonyl, arylaminocarbonylalkoxycarbonyl, N-alkyl-N-arylaminocarbonylalkoxycarbonyl, pyrrolidinylcarbonyl, piperidinylcarbonyl, morpholinylcarbonyl, piperazinylcarbonyl, aryloxycarbonyl, aralkyloxycarbonyl, heterocyclylalkoxycarbonyl, arylthiocarbonyl, aralkylthiocarbonyl, arylaminocarbonyl, aralkylaminocarbonyl, N-alkyl-N-arylaminocarbonyl, arylhydrazinocarbonyl, alkylhydrazinocarbonyl and phthalimidoxycarbonyl, each of which is optionally substituted, or $R^{10}$ together with $R^9$ represents the group $—CO—O—(CH_2)_n—$ where n represents the numbers 1 to 4, Y represents oxygen, sulphur, imino (NH) or alkylimino (N-alkyl), and Z represents nitrogen or the group $C—R^{11}$, where $R^{11}$ represents hydrogen, halogen, alkyl or alkoxy.

The new substituted cyclohexenes of the general formula (I) are obtained when cycloalkenes of the general formula (II)

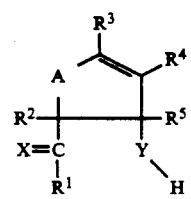

in which

A, $R^1$, $R^2$, $R^3$, $R^4$, $R^5$, X and Y have the abovementioned meanings, are reacted with azines of the general formula (III)

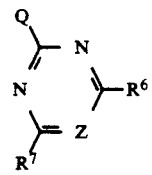

in which $R^6$, $R^7$ and Z have the abovementioned meanings and

Q represents a nucleofugic leaving group, if appropriate in the presence of an acid acceptor and if appropriate in the presence of a diluent.

The new substituted cycloalkenes are distinguished by a powerful herbicidal action.

The invention preferably relates to compounds of the formula (I) in which

A represents straight-chain or branched alkanediyl which has 1 to 5 carbon atoms and which is optionally substituted by hydroxyl, amino, halogen, phenyl or $C_1$–$C_5$-alkoxy-carbonyl, $R^1$ represents hydrogen, hydroxyl, amino, or a radical from the series comprising $C_1$–$C_5$-alkyl, $C_1$–$C_5$-alkoxy, $C_1$–$C_5$-alkylthio, $C_1$–$C_5$-alkylamino or di- ($C_1$–$C_5$-alkyl) amino, each of which is optionally substituted by halogen, $C_1$–$C_5$-alkoxy or oxiranyl, $R^2$, $R^3$, $R^4$ and $R^5$ are identical or different and represent hydrogen, hydroxyl, amino, cyano, halogen, $C_1$–$C_5$-alkyl, $C_1$–$C_5$-alkoxy, $C_1$–$C_5$-alkylthio, phenyl or $C_1$–$C_5$-alkoxycarbonyl, $R^6$ and $R^7$ are identical or different and represent hydrogen, halogen, or a radical from the series comprising $C_1$–$C_4$-alkyl, $C_1$–$C_4$-alkoxy, $C_1$–$C_4$-alkylthio, $C_1$–$C_4$-alkylamino or di-($C_1$–$C_4$-alkyl)-amino, each of which is optionally substituted by halogen or $C_1$–$C_3$-alkoxy, X represents oxygen, sulphur or one of the groups below $$N-R^8 \text{ or } C\diagup_{R^{10}}^{R^9}$$

where $R^8$ represents hydrogen, hydroxyl, amino, or a radical from the series comprising $C_1$-$C_6$-alkyl, $C_3$-$C_6$-alkenyl, $C_3$-$C_6$-alkynyl, $C_1$-$C_6$-alkoxy, $C_3$-$C_6$-alkenyloxy, $C_1$-$C_4$-alkoxy-carbonyl-$C_1$-$C_2$-alkoxy, $C_1$-$C_6$-alkylamino, di- ($C_1$-$C_2$-alkyl) -amino, $C_1$-$C_6$-alkylcarbonylamino, $C_1$-$C_6$-alkoxycarbonylamino, $C_1$-$C_6$-alkylsulphonylamino, each of which is optionally substituted by halogen, or represents a radical from the series comprising phenyl, phenyl-$C_1$-$C_4$-alkyl, phenoxy, phenyl-$C_1$-$C_4$-alkoxy, phenylamino, phenyl-$C_1$-$C_4$-alkylamino, N-($C_1$-$C_4$-alkyl) -N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, amino, cyano, carboxyl, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$-alkoxy-carbonyl and/or di-($C_1$-$C_2$-alkyl) -amino, $R^9$ represents hydrogen, halogen, cyano, carboxyl, $C_1$-$C_6$-alkoxycarbonyl, $C_1$-$C_6$-alkylcarbonylamino or di-($C_1$-$C_4$-alkoxy)-phosphoryl, and $R^{10}$ represents formyl, cyano, carboxyl, hydroxymethyl, carbamoyl, or a radical from the series comprising $C_1$-$C_6$-alkoxycarbonyl, $C_5$-$C_6$-cycloalkyloxycarbonyl, $C_1$-$C_6$-alkylthio-carbonyl, $C_5$-$C_6$-cycloalkylaminocarbonyl, di-($C_1$-$C_2$-alkyl)-aminocarbonyl, $C_1$-$C_4$-alkylaminocarbonyl-$C_1$-$C_4$-alkoxycarbonyl, di-($C_1$-$C_2$alkyl)-aminocarbonyl-$C_1$-$C_4$-alkoxycarbonyl, phenylaminocarbonyl-$C_1$-$C_4$-alkoxycarbonyl or N-methyl-N-phenylaminocarbonyl-$C_1$-$C_4$-alkoxy-carbonyl, each of which is optionally substituted by halogen, carboxyl or $C_1$-$C_4$-alkoxycarbonyl, or represents a radical from the series comprising pyrrolidinylcarbonyl, piperidinylcarbonyl, morpholinylcarbonyl or piperazinylcarbonyl, each of which is optionally substituted by methyl and/or ethyl, or represents a radical from the series comprising phenoxycarbonyl, phenyl-$C_1$-$C_4$-alkoxycarbonyl, furylmethoxycarbonyl, thienylmethoxycarbonyl, phenylthiocarbonyl, phenyl-$C_1$-$C_4$-alkylthio-carbonyl, phenylaminocarbonyl, phenyl-$C_1$-$C_4$-alkylaminocarbonyl, N-($C_1$-$C_4$-alkyl) -N-phenylaminocarbonyl or phenylhydrazinocarbonyl, $C_1$-$C_4$-alkylhydrazinocarbonyl, each of which is optionally substituted by nitro, amino, cyano, carboxyl, halogen, $C_1$-$C_4$-alkyl, $C_1$-$C_2$-halogenoalkyl, $C_1$-$C_4$-alkoxy, $C_1$-$C_2$-halogenoalkoxy, $C_1$-$C_4$-alkylthio, $C_1$-$C_2$-halogenoalkylthio, $C_1$-$C_4$- alkoxy-carbonyl and/or di- ($C_1$-$C_2$-alkyl)-amino, or represents phthalimidoxycarbonyl, or together with $R^9$ represents the group $-CO-O-(CH_2)_n-$ where n represents the numbers 1 to 4, Y represents oxygen, sulphur, imino (NH) or methylimino (NCH$_3$) and Z represents nitrogen or the group C—$R^{11}$, where $R^{11}$ represents hydrogen, fluorine, chlorine, methyl or methoxy.

The aliphatic hydrocarbon radicals which have been mentioned in the definition of the compounds according to the invention (for example alkyl, alkenyl or alkynyl), also as a combination with hetero atoms (for example in alkoxy, alkylthio, alkylamino) or in composite formulae such as, for example, halogenoalkyl or halogenoalkoxy, are in each case straight-chain or branched.

Halogen generally represents fluorine, chlorine, bromine or iodine, preferably fluorine, chlorine or bromine, in particular fluorine or chlorine.

In particular, the invention relates to compounds of the formula (I) in which

A represents methane-1,1-diyl (methylene, —CH$_2$—),
ethane-1,1-diyl (ethylidene, $$-\underset{CH_3}{\overset{|}{CH}}-),$$

ethane-1,2-diyl (dimethylene, —CH$_2$CH$_2$—),
propane-1,1-diyl (propylidene, $$-\underset{C_2H_5}{\overset{|}{CH}}-),$$

propane-1,2-diyl $$(-\underset{CH_3}{\overset{|}{CH}}CH_2-, \quad -CH_2-\underset{CH_3}{\overset{|}{CH}}-)$$

2-methyl-propane-1,2-diyl $$(-\underset{CH_3}{\overset{CH_3}{\overset{|}{\underset{|}{C}}}}-CH_2-, \quad -CH_2-\underset{CH_3}{\overset{CH_3}{\overset{|}{\underset{|}{C}}}}-),$$

propane-1,3-diyl (trimethylene, —CH$_2$CH$_2$CH$_2$—),
butane-1,2-diyl $$(-\underset{C_2H_5}{\overset{|}{CH}}-CH_2-, \quad -CH_2-\underset{C_2H_5}{\overset{|}{CH}}-)$$

or
butane-2,3-diyl $$(-\underset{CH_3}{\overset{|}{CH}}-\underset{CH_3}{\overset{|}{CH}}-),$$

$R^1$ represents hydrogen, hydroxyl, amino, or a radical from the series comprising methyl, ethyl, propyl, isopropyl, methoxy, oxiranylmethoxy, ethoxy, propoxy, isopropoxy, methylamino, ethylamino, propylamino, isopropylemino, dimethylamino or diethylamino, each of which is optionally substituted by fluorine, chlorine, methoxy or ethoxy, $R^2$, $R^3$, $R^4$ and $R^5$ are identical or different and represent hydrogen, hydroxyl, amino, fluorine, chlorine, bromine, methyl, ethyl, propyl, isopropyl, phenyl, methoxycarbonyl or ethoxycarbonyl, $R^6$ and $R^7$ are identical or different and represent hydrogen, chlorine, methyl, ethyl, trifluoromethyl, methoxymethyl, methoxy, ethoxy, difluoromethoxy, methylthio, methylamino, ethylamino or dimethylamino, X represents oxygen, sulphur or one of the groups below $$N-R^8 \text{ or } C\begin{smallmatrix}R^9\\R^{10}\end{smallmatrix}$$

where $R^8$ represents hydrogen, hydroxyl, amino, methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino, sec-butylamino, tert-butylamino, dimethylamino, acetylamino, propionylamino, methoxycarbonylacetylamino, ethoxycarbonylamino, methylsulphonylamino or ethylsulphonylamino, or represents phenyl, benzyl, phenoxyl benzyloxy, phenylamino, benzylamino, N-methyl-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, cyano, fluorine, chlorine, bromine, methyl, trifluoromethyl, methoxy, trifluoromethoxy, methylthio or trifluoromethylthio, $R^9$ represents hydrogen, fluorine, chlorine, cyano, carboxyl, $C_1$-$C_4$-alkoxycarbonyl, $C_1$-$C_4$-alkylcarbonylamino, dimethoxyphosphoryl or diethoxyphosphoryl and $R^{10}$ represents formyl, cyano, carboxyl, hydroxymethyl, carbamoyl, or represents a radical from the series comprising $C_1$-$C_4$-alkoxycarbonyl, $C_5$-$C_6$-cycloalkyloxycarbonyl, $C_1$-$C_4$-alkylthiocarbonyl, $C_1$-$C_4$-alkylaminocarbonyl, $C_5$-$C_6$-cycloalkylaminocarbonyl, dimethylaminocarbonyl, $C_1$-$C_4$-alkylaminocarbonyl-$C_1$-$C_4$-alkoxycarbonyl, dimethylaminocarbonyl-$C_1$-$C_4$-alkoxycarbonyl or N-methyl-N-phenylaminocarbonyl-$C_1$-$C_4$-alkoxycarbonyl, each of which is optionally substituted by fluorine, chlorine, carboxy or $C_1$-$C_4$-alkoxycarbonyl, or represents a radical from the series comprising pyrrolidinylcarbonyl, piperidinylcarbonyl, morpholinylcarbonyl or piperazinylcarbonyl, each of which is optionally substituted by methyl and/or ethyl, or represents a radical from the series comprising phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl or phenylhydrazinocarbonyl, each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or together with $R^9$ represents the groups —CO—O—CH$_2$CH$_2$—, —COO—CH$_2$CH$_2$CH$_2$—, $$-COO-CH_2-\underset{CH_3}{\underset{|}{CH}}- \text{ or } -COO-\underset{CH_3}{\underset{|}{CH}}-CH_2-,$$

Y represents oxygen or imino (NH) and

Z represents nitrogen or a CH group.

The compounds of the formula (I) in which
A represents
methane-1,1-diyl (methylene, —CH$_2$—),
ethane-1,1-diyl (ethylidene, $$-\underset{CH_3}{\underset{|}{CH}}-),$$

ethane-1,2-diyl (dimethylene, —CH$_2$—CH$_2$—),
propane-1,1-diyl (propylidene, $$-\underset{C_2H_5}{\underset{|}{CH}}-),$$

propane-1,2-diyl $$(-\underset{CH_3}{\underset{|}{CH}}CH_2-, \quad -CH_2-\underset{CH_3}{\underset{|}{CH}}-)$$

2-methyl-propane-1,2-diyl $$(-\underset{CH_3}{\overset{CH_3}{\underset{|}{\overset{|}{C}}}}-CH_2-, \quad -CH_2-\underset{CH_3}{\overset{CH_3}{\underset{|}{\overset{|}{C}}}}-),$$

propane-1,3-diyl (trimethylene, —CH$_2$CH$_2$CH$_2$—)
butane-1,2-diyl $$(-\underset{C_2H_5}{\underset{|}{CH}}-CH_2-, \quad -CH_2-\underset{C_2H_5}{\underset{|}{CH}}-)$$

or
butane-2,3-diyl $$(-\underset{CH_3}{\underset{|}{CH}}-\underset{CH_3}{\underset{|}{CH}}-),$$

$R^1$ represents hydroxyl, methoxy or ethoxy,
$R^2$ represents hydrogen, fluorine or methyl,
$R^3$ represents hydrogen or methyl,
$R^4$ represents hydrogen or methyl,
$R^5$ represents hydrogen or methyl,
$R^6$ represents hydrogen, methyl or methoxy,
$R^7$ represents methyl or methoxy,
X represents oxygen,
Y represents oxygen and
Z represents nitrogen or a CH group, must be particularly emphasised.

if, for example, methyl 2-hydroxy-3-cyclohexene-1-carboxylate and 2-chloro-4,6-dimethoxy-s-triazine are used as starting materials for the preparation process according to the invention, the course of the reaction can be represented by the following equation:

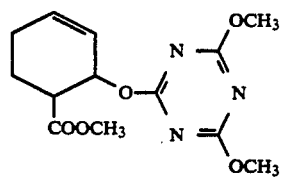

Formula (II) provides a general definition of the cyclohexanes to be used as starting materials in the process according to the invention for the preparation of compounds of the formula (I).

In formula (II), A, $R^1$, $R^2$, $R^3$, $R^4$, X and Y preferably, or in particular, have those meanings which have already been mentioned above in connection with the description of the compounds of the formula (I) according to the invention as being preferred, or particularly preferred, for A, $R^1$, $R^2$, $R^3$, $R^4$, $R^5$, X and Y.

Examples of the starting materials of the formula (II) are mentioned in Table 1 below.

TABLE 1

Examples of the starting materials of the formula (II) (II)

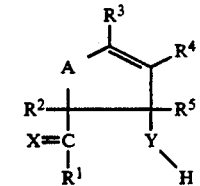

| A | $R^1$ | $R^2$ | $R^3$ | $R^4$ | $R^5$ | X | Y |
|---|---|---|---|---|---|---|---|
| —CH$_2$— | OH | H | H | H | H | O | O |
| —CH$_2$CH$_2$— | OH | H | H | H | H | O | O |
| —CH—<br>\|<br>CH$_3$ | OH | H | H | H | H | O | O |
| —CH—CH$_2$—<br>\|<br>CH$_3$ | OH | H | H | H | H | O | O |
| —CH$_2$—C(CH$_3$)$_2$— | OH | H | H | H | H | O | O |
| —C(CH$_3$)$_2$—CH$_2$— | CH$_3$ | H | H | H | CH$_3$ | O | O |
| —C(CH$_3$)(OC$_2$H$_5$)—CH$_2$— | OC$_2$H$_5$ | H | H | H | CH$_3$ | O | O |
| —CH$_2$CH$_2$— | OCH$_3$ | H | H | H | H | O | O |
| —CH$_2$CH$_2$— | OCH$_3$ | CH$_3$ | H | H | H | O | O |
| —CH$_2$CH$_2$— | H | CH$_3$ | CH$_3$ | H | H | O | O |
| —CH—CH$_2$—<br>\|<br>CH$_3$ | OCH$_3$ | CH$_3$ | H | H | H | O | O |
| —CH$_2$CH$_2$— | OCH$_3$ | H | CH$_3$ | H | H | O | O |

TABLE 1-continued

Examples of the starting materials of the formula (II) (II)

| A | $R^1$ | $R^2$ | $R^3$ | $R^4$ | $R^5$ | X | Y |
|---|---|---|---|---|---|---|---|
| —CH—CH$_2$—<br>\|<br>CH$_3$ | OCH$_3$ | H | H | H | H | O | NH |
| —CH$_2$CH$_2$— | OCH$_3$ | H | H | H | H | O | NH |
| —CH$_2$CH$_2$— | OCH$_3$ | CH$_3$ | H | H | H | O | NH |
| —CH—CH$_2$—<br>\|<br>CH$_3$ | OC$_2$H$_5$ | H | H | H | H | O | NH |
| —CH—CH$_2$—<br>\|<br>CH$_3$ | OCH$_3$ | H | H | H | H | O | NH |

The starting materials of the formula (III) are known and/or can be prepared by processes known per se (compare DE-OS (German Published Specification) 2,240,311; J. Org. Chem. 43 (1978), 3314–3319; loc. cit. 45 (1980), 2479–2581; J. Chem. Soc., Perkin I, 1981, 1096–1102; Chem. Pharm. Bull 34 (1986), 3488–3491; Tetrahedron Lett. 28 (1987), 4169–4172; EP-A 376,072).

Formula (III) provides a general definition of the azines furthermore to be used as starting materials in the process according to the invention for the preparation of compounds of the formula (I).

In formula (III), $R^6$, $R^7$ and Z preferably, or in particular, have those meanings which have already been mentioned above in connection with the description of the compounds of the formula (I) according to the invention as being preferred, or particularly preferred, for $R^6$, $R^7$ and Z, and Q preferably represents fluorine, chlorine, bromine or $C_1$-$C_4$-alkylsulphonyl, in particular chlorine or methylsulphonyl.

The following may be mentioned as examples of the starting materials of the formula (III):

2-Chloro-4,6-dimethyl-pyrimidine, 2-chloro-4-methyl-6-methoxy-pyrimidine, 2-chloro-4,6-dimethoxy-pyrimidine, 2-chloro-4-methyl-6-ethoxy-pyrimidine, 2,4-dichloro-6-methoxy-pyrimidine, 2-chloro-methyl-pyrimidine, 2,4-dichloro-6-methyl-pyrimidine, 2-chloro-4-trifluoromethyl-6-methoxy-pyrimidine, 2-chloro-4-methoxy-6-difluoromethoxy-pyrimidine, 2-chloro-4-methyl-6-difluoromethoxy-pyrimidine, 2-chloro-4,6-bis-difluoromethoxypyrimidine, 2,4-dichloro-6-ethoxy-pyrimidine, 2-chloro-4,6-diethoxy-pyrimidine, 2,4,5-trichloro-6-methylpyrimidine, 2,5-dichloro-4-methyl-6-methoxy-pyrimidine, 2,4,6-trichloro-pyrimidine, 2-chloro-4-ethyl-6-methoxypyrimidine, 2,5-dichloro-4,6-dimethoxy-pyrimidine, 2-chloro-4-methoxy-6-methylamino-pyrimidine and 2-chloro-4,6-bis-trifluoromethyl-pyrimidine, 2-chloro-4,6-dimethyl-s-triazine, 2-chloro-4-methoxy-6-methyl-s-triazine, 2-chloro-4,6-dimethoxy-s-triazine, 2-chloro-4-ethoxy-6-methyl-s-triazine and 2-chloro-4-ethyl-6-methoxy-s-triazine, and 2-methylsulphonyl-4,6-dimethyl-pyrimidine, 2-methylsulphonyl-4-methyl-6-methoxypyrimidine, 2-methylsulphonyl-4,6-dimethoxy-pyrimidine, 2-methylsulphonyl-4-methyl-6-ethoxy-pyrimidine, 2-methylsuphonyl-4-chloro-6-methoxy-pyrimidine, 2-methylsulphonyl-4-methylpyrimidine, 2-methylsulphonyl-4-chloro-6-methylpyrimidine, 2-methylsulphonyl-4-trifluoromethyl-6-methoxy-pyrimidine, 2-methylsulphonyl-4-methoxy-6-difluoromethoxy-pyrimidine, 2-methylsulphonyl-4-methyl-6-difluoromethoxy-pyrimidine, 2-methylsulphonyl-4,6-bis-difluoromethoxypyrimidine, 2-methylsulphonyl-4-chloro-6-ethoxypyrimidine, 2-methylsulphonyl-4,6-diethoxypyrimidine, 2-methylsulphonyl-4,5-dichloro-6-methylpyrimidine, 2-methylsulphonyl-4-methyl-5-chloro-6-methoxypyrimidine, 2-methylsulphonyl-4,6-dichloropyrimidine, 2-methylsulphonyl-4-ethyl-6-methoxypyrimidine, 2-methylsulphonyl-5-chloro-4,6-dimethoxypyrimidine, 2-methylsulphonyl-4-methoxy-6-methylaminopyrimidine and 2-methylsulphonyl-4,6-bis-trifluoromethyl-pyrimidine.

The azines of the formula (III) are known and/or can be prepared by processes known per se (cf. J. Chem. Soc. 1957, 1830, 1833; J. Org. Chem. 26 (1961), 792; U.S. Pat. No. 3,308,119; U.S. Pat. No. 4,711,959).

The process according to the invention for the preparation of the new compounds of the formula (I) is preferably carried out using diluents. Diluents which are suitable for this purpose are inert organic solvents. There preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobdnzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoric triamide.

Acid acceptors which can be employed in the process according to the invention are all acid-binding agents which can customarily be employed for reactions of this type. The following are preferably suitable: alkali metal hydroxides such as, for example, sodium hydroxide and potassium hydroxide, alkaline earth metal hydroxides such as, for example, calcium hydroxide, alkali metal carbonates and alkali metal alcoholates such as sodium carbonate and potassium carbonate, sodium tert-butylate and potassium tert-butylate, furthermore aliphatic, aromatic or heterocyclic amines, for ex ample triethylamine, trimethylamine, dimethylaniline, dimethylbenzylamine, pyridine, 1, 5-diazabicyclo-[4, 3, 0 ]-non-5-ene (DBN), 1,8-diazabicyclo-[5,4,0]-undec-7-ene (DBU) and 1,4-diazabicyclo-[2,2,2]-octane (DABCO).

When carrying out the process according to the invention, the reaction temperatures can be varied within a substantial range. In general, the process is carried out at temperatures between 0° C. and 150° C., preferably at temperatures between 10° C. and 100° C.

The process according to the invention is generally carried out under atmospheric pressure. However, it is also possible to carry out the process under increased or reduced pressure.

For carrying out the process according to the invention, the starting materials required in each case are generally employed in approximately equimolar amounts. However, it is also possible to use one of the two components employed in each case in a larger excess. The reactions are generally carried out in a suitable diluent in the presence of an acid acceptor, and the reaction mixture is stirred for several hours at the temperature required in-each case. Working-up is carried out in the process according to the invention in each case by customary methods (compare the Preparation Examples).

The active compounds according to the invention can be used as defoliants, desiccants, agents for destroying broad-leaved plants and, especially, as weed-.killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the aenera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The compounds of the formula (I) according to the invention are suitable for combating monocotyledon and dicotyledon weeds both by the pre- and the post-emergence method.

The active compounds can be converted into the customary formulations, such as solutions, emulsions, wettable powders, suspensions, powders, dusting agents, pastes, soluble powders, granules, suspensionemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example, anilides such as, for example, diflufenican and propanil; aryl carboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoates such as, for example, diclofop-methyl, fenoxaprop-ethyl, fluazifopbutyl, haloxyfop-methyl and quizalofop-ethyl; azinones such as, for example, chloridazon and norflurazon; carbamates such as, for example, chlorpropham, desmedipham, pherlmedipham and propham; chloroacetanilides such as, for example, alachlor, acetochlor, butachlor, metazachlor, metolachlor, pretilachlor and propachlor; dinitroanilines such as, for example, oryazalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxyl amines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuronethyl, chlorsulfuron, cinosulfuron, metsulfuron-methyl, nicosulfuron, primisulfuron, pyrazosulfuron-ethyl, thifensulfuron-methyl, triasulfuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyandzine, simazine, simetryne, terbutryne and terbutylazine; triazinones such as, for example, hexazinone, metamitron and metribuzin; others such as, for example, aminotriazol, benfuresate, bentazone, cirlmethylin, clomazone, clopyralid, difenzoquat, dithiopyr, ethofumesate, fluorochloridone, glufosinate, glyphosate, isoxaben, pyridate, quinchlorac, quimnerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

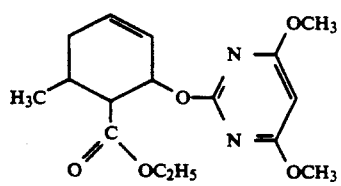

A mixture of 1.2 g (5.5 mmol) of 4,6-dimethoxy-2-methylsulphonyl-pyrimidine, 1.0 g (8.2 mmol) of ethyl 3-hydroxy-5-methylcyclohexene-4-carboxylate, 1.1 g (5.5 mmol) of potassium carbonate and 20 ml of acetonitrile is refluxed for 12 hours and subsequently concentrated. The residue is extracted by shaking with water-/ethyl acetate, and the organic phase is separated off, dried with sodium sulphate and filtered. The solvent is removed from the filtrate by distillation under a water pump vacuum.

1.2 g (71 % of theory) of ethyl 3-(4,6-dimethoxypyrimidin-2-yloxy)-5-methylcyclohexene-4-carboxylate are obtained as an oily residue.

Other compounds of the formula (I)

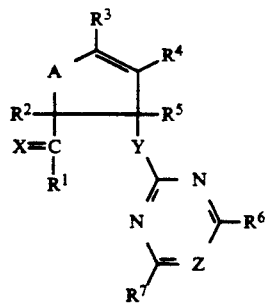

which can be prepared analogously to Example 1 and following the general description of the preparation process according to the invention are, for example, those listed in Table 2 below:

TABLE 2

Examples of the compounds of the formula (I)

| Ex. No. | A | $R^1$ | $R^2$ | $R^3$ | $R^4$ | $R^5$ | $R^6$ | $R^7$ | X | Y | Z | Physical Data |
|---|---|---|---|---|---|---|---|---|---|---|---|---|
| 2 | —CHCH$_2$—<br>\|<br>CH$_3$ | OH | H | H | H | H | OCH$_3$ | OCH$_3$ | O | O | CH | (oil) |
| 3 | —CH—CH$_2$—<br>\|<br>C$_6$H$_5$ | OH | H | H | H | H | OCH$_3$ | OCH$_3$ | O | O | CH | (oil) |
| 4 | —CH—CH$_2$—<br>\|<br>COOCH$_3$ | OCH$_3$ | H | H | H | H | OCH$_3$ | OCH$_3$ | O | O | CH | (oil) |
| 5 | —CH$_2$—CH$_2$— | OCH$_3$ | H | H | H | H | OCH$_3$ | OCH$_3$ | O | O | CH | (oil) |
| 6 | —CH$_2$—CH$_2$— | OH | H | H | H | H | OCH$_3$ | OCH$_3$ | O | O | CH | (oil) |
| 7 | —CH$_2$—CH$_2$— | OC$_2$H$_5$ | H | H | H | H | OCH$_3$ | OCH$_3$ | O | O | CH | (oil) |
| 8 | —CH$_2$—CH$_2$— | OCH$_2$-furyl | H | H | H | H | OCH$_3$ | OCH$_3$ | O | O | CH | (oil) |
| 9 | —CH$_2$—CH$_2$— | OC(CH$_3$)$_3$ | H | H | H | H | OCH$_3$ | OCH$_3$ | O | O | CH | (oil) |
| 10 | —CH$_2$—CH$_2$— | OC$_2$H$_5$ | CH$_3$ | H | H | H | OCH$_3$ | OCH$_3$ | O | O | CH | m.p. 65° C. |
| 11 | —CH$_2$—CH$_2$— | OH | CH$_3$ | H | H | H | OCH$_3$ | OCH$_3$ | O | O | CH | (oil) |
| 12 | —CH$_2$—CH$_2$— | OC$_4$H$_9$ | F | H | H | H | OCH$_3$ | OCH$_3$ | O | O | CH | (oil) |
| 13 | —CH$_2$—CH$_2$— | OH | F | H | H | H | OCH$_3$ | OCH$_3$ | O | O | CH | m.p. 145° C. |
| 14 | —CH$_2$—CH$_2$— | OCH$_3$ | —CH$_2$COOCH$_3$ | H | H | H | OCH$_3$ | OCH$_3$ | O | O | CH | m.p. 95° C. |
| 15 | —CH$_2$—CH$_2$— | OH | —CH$_2$COOCH$_3$ | H | H | H | OCH$_3$ | OCH$_3$ | O | O | CH | (oil) |
| 16 | —CH—CH$_2$<br>\|<br>CH$_3$ | OC$_2$H$_5$ | H | H | H | H | Cl | OCH$_3$ | O | O | CH | (oil) |
| 17 | —CH—CH$_2$<br>\|<br>CH$_3$ | OH | H | H | H | H | Cl | OCH$_3$ | O | O | CH | (oil) |
| 18 | —CH$_2$—CH$_2$ | OC$_2$H$_5$ | H | H | H | H | Cl | OCH$_3$ | O | O | CH | (oil) |
| 19 | —CH$_2$—CH$_2$— | OH | H | H | H | H | Cl | OCH$_3$ | O | O | CH | (oil) |
| 20 | —CH$_2$—CH$_2$— | OCH$_3$ | CF$_3$ | H | H | H | OCH$_3$ | OCH$_3$ | O | O | CH | (oil) |
| 21 | —CH—CH$_2$—<br>\|<br>CH$_3$ | OC$_2$H$_5$ | H | H | H | H | OCH$_3$ | OCH$_3$ | O | O | CH | (oil) |

STARTING MATERIALS OF THE FORMULA (II)

Example (II-1)

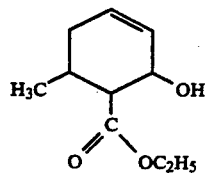

5.0 g (27.4 mmol) of ethyl 5-methyl-3-oxocyclohexene-4-carboxylate are introduced into 40 ml of methanol, and the mixture is cooled to 0° C. and treated with 10.2 g (27.4 mmol) of cerium(III) chloride heptahydrate and 1.1 g (27.4 mmol) of sodium borohydride. The mixture is stirred for two hours at room temperature and then poured into water and extracted with dichloromethane. The combined organic phases are dried with sodium sulphate and filtered. The filtrate is concentrated.

4.6 g (92% of theory) of ethyl 3-hydroxy-5-methylcyclohexene-4-carboxylate are obtained as an oily residue.

Example A

| Pre-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The tables denote:

0% = no action (like untreated control)
100% = total destruction

In this test, the compounds according to Preparation Examples 1 and 2 show a very powerful action against weeds.

Example B

Post-emergence Test

| Post-emergence test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, the compounds according to Preparation Examples 1 and 2 show a very powerful action against weeds.

It will be understood that the specification and examples are illustrative but not limitative of the present invention and that other embodiments within the spirit and scope of the invention will suggest themselves to those skilled in the art.

We claim:

1. A substituted cycloalkene of the formula

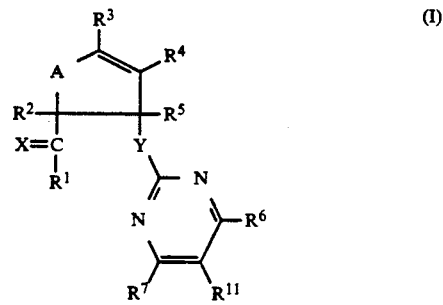

in which
A represents straight-chain or branched alkanediyl which has 1 to 5 carbon atoms and which is optionally substituted by hydroxyl, amino, halogen, phenyl or $C_1$-$C_5$-alkoxy-carbonyl,
$R^1$ represents hydrogen, hydroxyl, amino, or a radical selected from the group consisting of $C_1$-$C_5$-alkyl, $C_1$-$C_5$-alkoxy, $C_1$-$C_5$-alkylthio, $C_1$-$C_5$-alkylamino or di-($C_1$-$C_5$-alkyl)-amino, each of which is optionally substituted by halogen, $C_1$-$C_5$-alkoxy and oxiranyl,
$R^2$, $R^3$, $R^4$ and $R^5$ are identical or different and represent hydrogen, hydroxyl, amino, cyano, halogen, $C_1$-$C_5$-alkyl, $C_1$-$C_5$-alkoxy, $C_1$-$C_5$-alkylthio, phenyl or $C_1$-$C_5$-alkoxycarbonyl,
$R^6$ and $R^7$ are identical or different and represent hydrogen, halogen, or a radical selected from the group consisting of $C_1$-$C_4$-alkyl, $C_1$-$C_4$-alkoxy, $C_1$-$C_4$-alkylthio, $C_1$-$C_4$-alkylamino and di-($C_1$-$C_4$-alkyl)-amino, each of which is optionally substituted by halogen or $C_1$-$C_3$-alkoxy,
X represents oxygen, sulphur or one of the groups

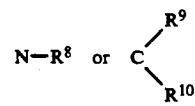

where

R⁸ represents hydrogen, hydroxyl, amino, or a radical selected from the group consisting of C₁–C₆-alkyl, C₃–C₆-alkenyl, C₃–C₆-alkynyl, C₁–C₆-alkoxy, C₁–C₆-alkenyloxy, C₁–C₄-alkoxy-carbonyl-C₁–C₂-alkoxy, C₁–C₆-alkylamino, di-(C₁–C₂-alkyl)-amino, C₁–C₆-alkylcarbonylamino, C₁–C₆-alkoxycarbonylamino, C₁–C₆-alkyl-sulphonylamino, each of which is optionally substituted by halogen, or represents a radical selected from the group consisting of phenyl, phenyl-C₁–C₄-alkyl, phenoxy, phenyl-C₁–C₄-alkoxy, phenylamino, phenyl-C₁–C₄-alkylamino, N-(C₁–C₄-alkyl)-N-phenylamino, pyridylamino, pyrimidylamino, pyridylcarbonylamino, phenylcarbonylamino, furylcarbonylamino, thienylcarbonylamino and phenylsulphonylamino, each of which is optionally substituted by nitro, amino, cyano, carboxyl, halogen, C₁–C₄-alkyl, C₁–C₂-halogenoalkyl, C₁–C₄-alkoxy, C₁–C₂-halogenoalkoxy, C₁–C₄-alkylthio, C₁–C₂-halogenoalkylthio, C₁–C₄-alkoxycarbonyl and/or di-(C₁–C₂-alkyl)-amino, R⁹ represents hydrogen, halogen, cyano, carboxyl, C₁–C₆-alkoxycarbonyl, C₁–C₆-alkylcarbonylamino or di-(C₁–C₄-alkoxy)-phosphoryl, and R¹⁰ represents formyl, cyano, carboxyl, hydroxymethyl, carbamoyl, or represents a radical selected from the group consisting of C₁–C₆-alkoxycarbonyl, C₅–C₆-cycloalkoxycarbonyl, C₁–C₆-alkylthiocarbonyl, alkylaminocarbonyl, C₅–C₆-cycloalkylaminocarbonyl, di-(C₁–C₂-alkyl)-aminocarbonyl, C₁–C₄-alkylaminocarbonyl-C₁–C₄-alkoxycarbonyl, di-(C₁–C₂-alkyl)-aminocarbonyl-C₁–C₄-alkoxycarbonyl, phenylaminocarbonyl-C₁–C₄-alkoxycarbonyl and N-methyl-N-phenylaminocarbonyl-C₁–C₄-alkoxycarbonyl, each of which is optionally substituted by halogen, carboxyl or C₁–C₄-alkoxycarbonyl, or represents a radical selected from the group consisting of pyrrolidinylcarbonyl, piperidinylcarbonyl, morpholinylcarbonyl and piperazinylcarbonyl, each of which is optionally substituted by methyl and/or ethyl, or represents a radical selected from the group consisting of phenoxycarbonyl, phenyl-C₁–C₄-alkoxycarbonyl, furylmethoxycarbonyl, thienylmethoxycarbonyl, phenylthiocarbonyl, phenyl-C₁–C₄-alkylthio-carbonyl, phenylaminocarbonyl phenyl-C₁–C₄-alkylaminocarbonyl, N-(C₁–C₄-alkyl)-N-phenylaminocarbonyl and phenylhydrazino-carbonyl, C₁–C₄-alkylhydrazinocarbonyl, each of which is optionally substituted by nitro, amino, cyano, carboxyl, halogen, C₁–C₄-alkyl, C₁–C₂-halogenoalkyl, C₁–C₄-alkoxy, C₁–C₂-halogenoalkoxy, C₁–C₄-alkoxycarbonyl and/or di-(C₁–C₂-alkyl)-amino, or represents phthalimidoxycarbonyl, or together with R⁹ stands for —CO—O—(CH₂)ₙ— where n represents the numbers 1 to 4, Y represents oxygen, sulphur, imino (NH) or methylimino (NCH₃) and R¹¹ represents hydrogen, fluorine, chlorine, methyl or methoxy.

2. A substituted cycloalkene according to claim 1, in which

A represents
methane-1,1-diyl (methylene, —CH₂—),
ethane-1,1-diyl (ethylidene,

ethane-1,2-diyl (dimethylene, —CH₂CH₂—),
propane-1,1-diyl (propylidene,

propane-1,2-diyl

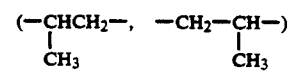

2-methyl-propane-1,2-diyl

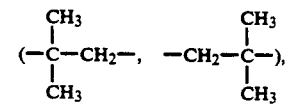

propane-1,3-diyl (trimethylene, —CH₂CH₂CH₂—),
butane-1,2-diyl

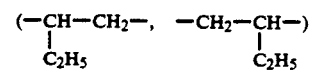

or
butane-2,3-diyl

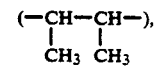

R¹ represents hydrogen, hydroxyl, amino, or a radical selected from the group consisting of methyl, ethyl, propyl, isopropyl, methoxy, oxiranylmethoxy, ethoxy, propoxy, isopropoxy, methylamino, ethylamino, propylamino, isopropylamino, dimethylamino and diethylamino, each of which is optionally substituted by fluorine, chlorine, methoxy or ethoxy, R², R³, R⁴ and R⁵ are identical or different and represent hydrogen, hydroxyl, amino, fluorine, chlorine, bromine, methyl, ethyl, propyl, isopropyl, phenyl, methoxycarbonyl or ethoxycarbonyl, R⁶ and R⁷ are identical or different and represent hydrogen, chlorine, methyl, ethyl, trifluoromethyl, methoxymethyl, methoxy, ethoxy, difluoromethoxy, methylthio, methylamino, ethylamino or dimethylamino, X represents oxygen, sulphur or one of the groups

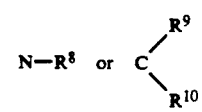

where
R⁶ represents hydrogen, hydroxyl, amino, methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino sec-butylamino, tert-butylamino, dimethylamino, acetylamino, propionylamino, methoxycarbonylamino, methylsulphonylamino or ethylsulphonylamino, or represents phenyl, benzyl, phenoxy, benzyloxy, phenylamino, benzylamino, N-methyl-N-phenylamino, pyridylamino, pyridylamino, pyridylcarbonylamino, phenylcarbonylamino, furylcarbonylamino, thienylcarbonylamino or phenylsulphonylamino, each of which is optionally substituted by nitro, cyano, fluorine, chlorine, bromine, methyl, trifluoromethyl, methoxy, trifluoromethoxy, methylthio or trifluoromethylthio, $R^9$ represents hydrogen, fluorine, chlorine, cyano, carbo-xyl, $C_1$-$C_4$-alkoxycarbonyl, $C_1$-$C_4$-alkylcarbonyl-amino, dimethoxyphosphoryl or diethoxyphosphoryl and $R^{10}$ represents formyl, cyano, carboxyl, hydroxymethyl, carbamoyl, or represents a radical selected from the group consisting of $C_1$-$C_4$-alkoxycarbonyl, $C_5$-$C_6$-cycloalkyloxycarbonyl, $C_1$-$C_4$-alkylthiocarbonyl, $C_1$-$C_4$-alkylaminocarbonyl, $C_5$-$C_6$-cycloalkylaminocarbonyl, dimethylaminocarbonyl, $C_1$-$C_4$-alkylaminocarbonyl-$C_1$-$C_4$-alkoxycarbonyl, dimethylaminocarbonyl-$C_1$-$C_4$-alkoxycarbonyl and N-methyl-N-phenylamino-carbonyl-$C_1$-$C_4$-alkoxycarbonyl, each of which is optionally substituted by fluorine, chlorine, carboxyl or $C_1$-$C_4$-alkoxycarbonyl, or represents a radical selected from the group consisting of pyrrolidinylcarbonyl, piperidinylcarbonyl, morpholinylcarbonyl and piperazinylcarbonyl, each of which is optionally substituted by methyl and/or ethyl, or represents a radical selected from the group consisting of phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl and phenylhydrazinocarbonyl, each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or together with $R^9$ represents the groups —CO—O—CH$_2$CH$_2$—, —COO—CH$_2$CH$_2$CH$_2$—, $$-COO-CH_2-\underset{\underset{CH_3}{|}}{CH}- \quad \text{or} \quad -COO-\underset{\underset{CH_3}{|}}{CH}-CH_2-,$$

and

Y represents oxygen or imino (NH).

3. A substituted cycloalkene according to claim 1, in which

A represents
methane-1,1-diyl (methylene, —CH$_2$—),
ethane-1,1-diyl (ethylidene, $$-\underset{\underset{CH_3}{|}}{CH}-),$$

ethane-1,2-diyl (dimethylene, —CH$_2$CH$_2$—),
propane-1,1-diyl (propylidene, $$-\underset{\underset{C_2H_5}{|}}{CH}-),$$

propane-1,2-diyl $$(-\underset{\underset{CH_3}{|}}{CH}CH_2-, \quad -CH_2-\underset{\underset{CH_3}{|}}{CH}-)$$

2-methyl-propane-1,2-diyl $$(-\underset{\underset{CH_3}{|}}{\overset{\overset{CH_3}{|}}{C}}-CH_2-, \quad -CH_2-\underset{\underset{CH_3}{|}}{\overset{\overset{CH_3}{|}}{C}}-),$$

propane-1,3-diyl (trimethylene, —CH$_2$CH$_2$CH$_2$—)
butane-1,2-diyl $$(-\underset{\underset{C_2H_5}{|}}{CH}-CH_2-, \quad -CH_2-\underset{\underset{C_2H_5}{|}}{CH}-)$$

or
butane-2,3-diyl $$(-\underset{\underset{CH_3}{|}}{CH}-\underset{\underset{CH_3}{|}}{CH}-),$$

$R^1$ represents hydroxyl, methoxy or ethoxy,
$R^2$ represents hydrogen, fluorine or methyl,
$R^3$ represents hydrogen or methyl,
$R^4$ represents hydrogen or methyl,
$R^5$ represents hydrogen or methyl,
$R^6$ represents hydrogen, methyl or methoxy,
$R^7$ represents methyl or methoxy,
X represents oxygen,
Y represents oxygen and
$R^{11}$ represents H.

4. A compound according to claim 1 wherein such compound is ethyl 3-(4,6-dimethoxy-pyrimidin-2-yloxy)-5-methylcyclohexene-4-carboxylate of the formula

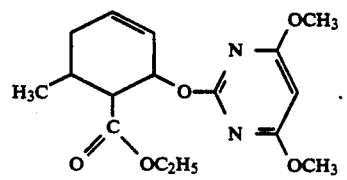

5. A compound according to claim 1 wherein such compound is 3-(4,6-dimethoxy-pyrimidin-2-yloxy)-5-methylcyclohexene-4-carboxylic acid of the formula

6. A compound according to claim 1 wherein such compound is 3-(4,6-dimethoxy-pyrimidin-2-yloxy)-5-phenylcyclohexene-4-carboxylic acid of the formula

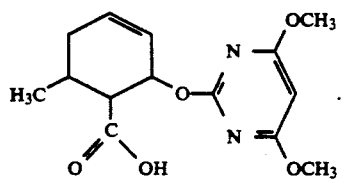

7. A compound according to claim 1 wherein such compound is methyl 3-(4,6-dimethoxy-pyrimidin-2-yloxy)-cyclohexene-4-carboxylate of the formula

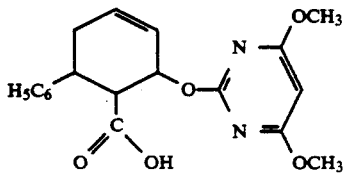

8. A compound according to claim 1 wherein such compound is 3-(4,6-dimethoxy-pyrimidin-2-yloxy)-cyclohexene-4-carboxylic acid of the formula

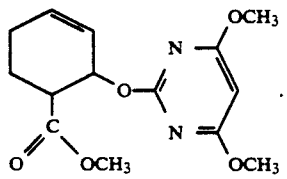

9. A compound according to claim 1 wherein such compound is ethyl 3-(4,6-dimethoxy-pyrimidin-2-yloxy)-cyclohexene-4-carboxylate of the formula

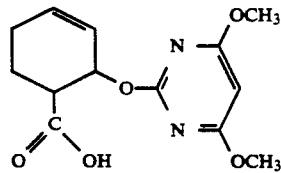

10. A compound according to claim 1 wherein such compound is glycidyl 3-(4,6-dimethoxy-pyrimidin-2-yloxy)-cyclohexene-4-carboxylate of the formula

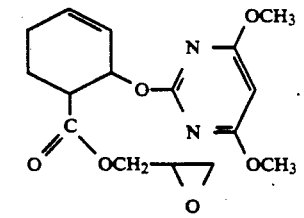

11. A compound according to claim 1 wherein such compound is n-butyl 3-(4,6-dimethoxy-pyrimidin-2-yloxy)-4-fluoro-4-carboxylate of the formula

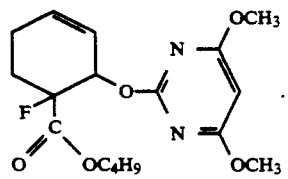

12. A compound according to claim 1 wherein such compound is 3-(4,6-dimethoxy-pyrimidin-2-yloxy)-4-fluoro-4-carboxylic acid of the formula

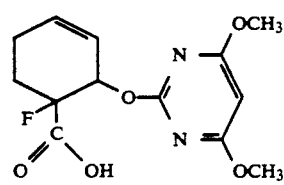

13. A compound according to claim 1 wherein such compound is ethyl 3-(4-chloro-5-methoxy-pyrimidin-2-yloxy)-cyclohexene-4-carboxylate of the formula

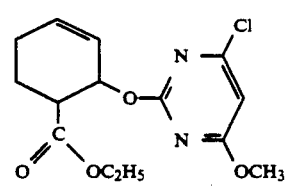

14. A compound according to claim 1 wherein such compound is methyl 3-(4,6-dimethoxy-pyrimidin-2-yloxy)-4-trifluoromethylcyclohexene-4-carboxylate of the formula

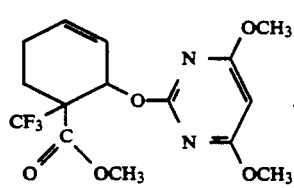

15. A herbicidal composition comprising a herbicidally effective amount of a compound according to claim 1 and a diluent.

16. A method of combating unwanted vegetation which comprises applying to such vegetation or to a locus from which it is desired to exclude such vegetation a herbicidally effective amount of a compound according to claim 1.

17. The method according to claim 16, wherein such compound is ethyl 3-(4,6-dimethoxy-pyrimidin-2-yloxy)-5-methyl-cyclohexene-4-carboxylate, 3-(4,6-dimethoxy-pyrimidin-2-yloxy)-5-methylcyclohexene-4-carboxylic acid, 3-(4,6-dimethoxy-pyrimidin-2-yloxy)-5-phenylcyclohexene-4-carboxylic acid, methyl 3-(4,6-dimethoxy-pyrimidin-2-yloxy)-cyclohexene-4-carboxylate, 3-(4,6-dimethoxy-pyrimidin-2yloxy)-cyclohexene-4-carboxylic acid, 3-(4,6-dimethoxy-pyrimidin-2yloxy)-cyclohexene-4-carboxylate, glycidyl 3-(4,6-dimethoxy-pyrimidin-2yloxy)-cyclohexene-4-carboxylate, n-butyl 3-(4,6-dimethoxy-pyrimidin-2yloxy)-4-fluoro-4-carboxylate, 3-(4,6-dimethoxy-pyrimidin-2yloxy)-4-fluoro-4-carboxylic acid, ethyl 3-(4,6-dimethoxy-pyrimidin-2yloxy)-cyclohexene-4-carboxylate or methyl 3-(4,6-dimethoxy-pyrimidin-2yloxy)-4-trifluoromethylcyclohexene-4-carboxylate.

* * * * *

UNITED STATES PATENT AND TRADEMARK OFFICE
CERTIFICATE OF CORRECTION

PATENT NO. : 5,284,820
DATED : February 8, 1994
INVENTOR(S) : Drewes, et al.

It is certified that error appears in the above-identified patent and that said Letters Patent is hereby corrected as shown below:

| | |
|---|---|
| Column 18, line 67, | cancel "$R^6$" and substitute --$R^8$-- |
| Column 19, lines 8 and 9, | after "methoxycarbonylamino" insert --ethoxycarbonylamino-- |
| Column 22, lines 37 and 38 | cancel "3-(4-chloro-5-methoxy-pyrimidin-2-yloxy)" and substitute --3-(4-chloro-6-methoxy-pyrimidin-2-yloxy -- |
| Column 24, line 3, | before "3-(4,6-dimethoxy-pyrimidin-2yloxy)" insert --ethyl-- |
| Column 24, lines 11, | cancel "3-(4,6-dimethoxy-pyrimidin-2yloxy)-cyclohexene-4-carboxylate" and substitute --3-(4-chloro-6-methoxy-pyrimidin-2-yloxy)-cyclohexene-4-carboxylate-- |

Signed and Sealed this

Sixteenth Day of February, 1999

Attest:

Attesting Officer

*Acting Commissioner of Patents and Trademarks*